(12) United States Patent
Bornhop et al.

(10) Patent No.: US 8,134,707 B2
(45) Date of Patent: Mar. 13, 2012

(54) ON-CHIP POLARIMETRY FOR HIGH-THROUGHPUT SCREENING OF NANOLITER AND SMALLER SAMPLE VOLUMES

(75) Inventors: Darryl J. Bornhop, Nashville, TN (US); Stephen Dotson, Nashville, TN (US); Brian O. Bachmann, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 690 days.

(21) Appl. No.: 11/666,046

(22) PCT Filed: Oct. 24, 2005

(86) PCT No.: PCT/US2005/038168
§ 371 (c)(1),
(2), (4) Date: Jul. 24, 2009

(87) PCT Pub. No.: WO2006/047408
PCT Pub. Date: May 4, 2006

(65) Prior Publication Data
US 2010/0027008 A1  Feb. 4, 2010

Related U.S. Application Data

(60) Provisional application No. 60/620,661, filed on Oct. 22, 2004.

(51) Int. Cl.
*G01J 4/00* (2006.01)
(52) U.S. Cl. .................................................... 356/364
(58) Field of Classification Search ........... 356/364–369
See application file for complete search history.

(56) References Cited

U.S. PATENT DOCUMENTS

| | | | | |
|---|---|---|---|---|
| 4,895,431 A | * | 1/1990 | Tsujiuchi et al. | |
| 4,976,154 A | | 12/1990 | Schneider et al. | |
| 4,990,925 A | * | 2/1991 | Edelsohn et al. | |
| 5,073,024 A | * | 12/1991 | Valette et al. | |
| 5,120,131 A | * | 6/1992 | Lukosz | 356/351 |

(Continued)

FOREIGN PATENT DOCUMENTS

EP    1746385 A1    1/2007

(Continued)

OTHER PUBLICATIONS

Abato, et al., "An enzymatic method for determining enantiomeric excess," *J Am Chem Soc*, 123:9206-9207 (2001).

(Continued)

*Primary Examiner* — Roy M Punnoose
(74) *Attorney, Agent, or Firm* — Ballard Spahr LLP (57) ABSTRACT

A polarimetry technique for measuring optical activity that is particularly suited for high throughput screening employs a chip or substrate (22) having one or more microfluidic channels (26) formed therein. A polarized laser beam (14) is directed onto optically active samples that are disposed in the channels. The incident laser beam interacts with the optically active molecules in the sample, which slightly alter the polarization of the laser beam as it passes multiple times through the sample. Interference fringe patterns (28) are generated by the interaction of the laser beam with the sample and the channel walls. A photodetector (34) is positioned to receive the interference fringe patterns and generate an output signal that is input to a computer or other analyzer (38) for analyzing the signal and determining the rotation of plane polarized light by optically active material in the channel from polarization rotation calculations.

23 Claims, 8 Drawing Sheets

U.S. PATENT DOCUMENTS

| | | | | |
|---|---|---|---|---|
| 5,268,305 | A * | 12/1993 | Ribi et al. | 436/501 |
| 5,273,633 | A * | 12/1993 | Wang et al. | |
| 5,325,170 | A * | 6/1994 | Bornhop | 356/128 |
| 5,479,257 | A * | 12/1995 | Hashimoto | |
| 5,485,312 | A * | 1/1996 | Horner et al. | |
| 5,502,561 | A * | 3/1996 | Hutchins | 356/336 |
| 5,613,013 | A * | 3/1997 | Schuette | |
| 5,659,318 | A * | 8/1997 | Madsen et al. | |
| 5,781,304 | A * | 7/1998 | Kotidis et al. | |
| 5,804,453 | A * | 9/1998 | Chen | |
| 5,817,462 | A * | 10/1998 | Garini et al. | |
| 5,915,034 | A * | 6/1999 | Nakajima et al. | |
| 5,953,439 | A * | 9/1999 | Ishihara et al. | |
| 5,995,645 | A * | 11/1999 | Soenksen et al. | |
| 6,108,458 | A * | 8/2000 | Hart | |
| 6,198,532 | B1 | 3/2001 | Cabib et al. | |
| 6,381,025 | B1* | 4/2002 | Bornhop et al. | 356/517 |
| 6,480,282 | B1 | 11/2002 | Chinowsky et al. | |
| 6,493,090 | B1* | 12/2002 | Lading et al. | 356/484 |
| 6,529,279 | B2* | 3/2003 | De Groot et al. | |
| 6,532,061 | B2* | 3/2003 | Ortyn et al. | |
| 6,533,914 | B1* | 3/2003 | Liu | 204/601 |
| 6,741,361 | B2* | 5/2004 | Marron | |
| 6,744,950 | B2* | 6/2004 | Aleksoff | |
| 6,798,509 | B2* | 9/2004 | Sonehara et al. | |
| 6,809,828 | B2* | 10/2004 | Bornhop et al. | 356/517 |
| 6,980,299 | B1* | 12/2005 | de Boer | |
| 7,130,060 | B2* | 10/2006 | Bornhop et al. | 356/517 |
| 7,173,986 | B2* | 2/2007 | Wu | 375/343 |
| 7,202,076 | B2* | 4/2007 | Cunningham et al. | |
| 7,300,803 | B2* | 11/2007 | Lin et al. | |
| 2004/0058058 | A1 | 3/2004 | Shchegolikhin et al. | |
| 2005/0014179 | A1 | 1/2005 | Karlsson et al. | |
| 2005/0190372 | A1 | 9/2005 | Dogariu | |
| 2005/0227374 | A1 | 10/2005 | Cunningham | |
| 2005/0244863 | A1 | 11/2005 | Mir | |
| 2006/0012800 | A1 | 1/2006 | Bornhop et al. | 356/517 |
| 2006/0039004 | A1 | 2/2006 | De Boer et al. | |
| 2006/0256343 | A1 | 11/2006 | Choma et al. | |
| 2007/0054339 | A1 | 3/2007 | Lin et al. | |

FOREIGN PATENT DOCUMENTS

| | | |
|---|---|---|
| EP | 08755681.7 | 5/2008 |
| FR | 2 766 922 A | 2/1999 |
| WO | WO 01/14858 | 3/2001 |
| WO | WO 2004/023115 | 3/2004 |
| WO | WO 2007/002178 | 1/2007 |

OTHER PUBLICATIONS

Adányi et al., "Development of immunosensor based on OWLS technique for determining Aflatoxin B1 and Ochratoxin A," *Biosens Bioelectron* 22:797-802 (2007).

Alunni, et al., "Mechanisms of inhibition of phenylalanine ammonia-lyase by phenol inhibitors and phenol/glycine synergistic inhibitors," *Arch Biochem and Biophys* 412(2):170-175 (2003).

Anderson, et al., "Fabrication of topologically complex three-dimensional microfluidic systems in PDMS by rapid prototyping," *Anal Chem* 72(14):3158-64 (2000).

Andersson et al., "TV shearography: quantitative measurement of shear-magnitude fields by use of digital speckle photography," Applied Optics, vol. 39:2565 (2000).

Anuta, "Digital Registration of Multispectral Video Imagery," Society of Photo-optical Instrumentation Engineers Journal, vol. 7:168 (1969).

Arnold, "Design by directed evolution," *Accounts Chem Res* 31(3):125-131 (1998).

Bobbitt, et al., "Direct and Indirect Polarimetry for Detection in Microbore Liquid-Chromatography," *Anal Chem* 56:1577-1581 (1984).

Borman, "Combinatorial chemistry," *Chem & Eng News* vol. 80 No. 45:43-57 (2002).

Bornhop, "Microvolume index of refraction determinations by interferometric backscatter," *Applied Optics*, vol. 34:3234-39 (1995).

Bornhop, et al., "Free-Solution, Label-Free Molecular Interactions Studied by Back-Scattering Interferometry," Science, vol. 317 No. 5485:1732-1736 (2007).

Bornhop, et al., "Polarimetry in capillary dimensions," *Anal Chem* 68:1677-1684 (1996).

Bouchara, "Efficient algorithm for computation of the second-order moment of the subpixel-edge position," Applied Optics, vol. 43:4550 (2004).

Brawer, et al., "Screening for prostatic carcinoma with prostate specific antigen," *J. Urol.*, 147:841-845 (1992).

Brenan, et al., "High throughput, nanoliter quantitative PCR," *Drug Discovery Today: Tech*, 2:247-253 (2005).

Brockhaus et al., "Thermadynamic studies on the interaction of antibodies with β-amyloid peptide," *J Phys Chem B*, 111:1238-43 (2007).

Brockman et al., "A Multistep Chemical Modification Procedure to Create DNA Arrays on Gold Surfaces for the Study of Protein—DNA Interactions with Surface Plasmon Resonance Imaging," *J Am Chem Soc*, vol. 121 issue 35:8044-8051 (1999).

Burke et al., "Stopped-flow enzyme assays on a chip using a microfabricated mixer," *Anal Chem*, 75(8):1786-1791 (2003).

Campitelli et al., "Shear horizontal surface acoustic wave based immunosensing system," *Int Conf on Solid State Sensors and Actuators*, Jun. 16-19, 1:187-190 (1997).

Choquette et al., "Wavenumber Standards for Near-infrared Spectrometry," Handbook of Vibrational Spectroscopy, John M. Chalmers and Peter R. Griffiths (Editors), 2002, p. 1-7.

Cohen, et al., "In vitro enzyme evolution: the screening challenge of isolating the one in a million," *Trends in Biotechnol*, 19:507-510 (2001).

Collignon et al., "Automated multimodality image registration based on information theory", Information Processing in Medical Imaging (Y. Bizais, C. Barillot and R. Di Paola, eds.), Kluwer Academic Publishers, Dordrecht, pp. 263-274, 1995.

Duffy et al., "Rapid prototyping of microfluidic systems in poly(dimethylsiloxane)," *Anal Chem*, 70:4974-4984 (1998).

Fan, et al., "Electrochemical interrogation of conformational changes as a reagentless method for the sequence-specific detection of DNA" *Proc Natl Acad Sci U S A*, 100(16): 9134-9137 (2003).

Finn, "Emerging methods for the rapid determination of enantiomeric excess," *Chirality*, 14:534-540 (2002).

Fox, et al., "Assay Innovations Vital to Improving HTS," *Drug Discovery and Development*, Mar. 2000:40-43.

Fricke-Begemann et al., "Speckle interferometry: three-dimensional deformation field measurement with a single interferogram," *Applied Optics*, vol. 40:5011 (2001).

Gibbs, et al., "Imaging polarimetry for high throughput chiral screening," *Biotech Progress*, 19:1329-1334 (2003).

Gloge, et al., "The behavior of substrate analogues and secondary deuterium isotope effects in the phenylalanine ammonia-lyase reaction," *Arch of Biochem and Biophys*, 359:1-7 (1998).

Gloge, et al., "Phenylalanine ammonia-lyase: The use of its broad substrate specificity for mechanistic investigations and biocatalysis—Synthesis of L-arylalanines," *Chemistry—A European Journal*, vol. 6, issue 18:3386-3390 (2000).

Grant No. R01 EB003537-01A2 awarded by National Institutes of Health.

Greisen, et al., "PCR primers and probes for the 16S rRNA gene of most species of pathogenic bacteria, including bacteria found in cerebrospinal fluid," *J Clin Microbiol*, 32:335-351 (1994).

Grosse, et al., "Deep wet etching of fused silica glass for hollow capillary optical leaky waveguides in microfluidic devices," *J Micromech and Microeng*, 11:257-262 (2001).

Guizar-Sicairos et al., "Efficient subpixel image registration algorithms," Optics Letters, vol. 33:156-158 (2008).

Guo, et al., "Measurement of enantiomeric excess by kinetic resolution and mass spectrometry," *Angew Chem Int Ed*, 38:1755-1758 (1998).

Harrison, et al., "Capillary Electrophoresis and Sample Injection Systems Integrated on a Planar Glass Chip," *Anal Chem*, 64(17):1926-1932 (1992).

Harteveld et al., "Detection of *Staphylococcal* Enterotoxin B employing a piezoelectric crystal immunosensor," *Biosens Bioelectron* 12(7):661-667 (1997).

Hodgins, "Yeast Phenylalanine Ammonia-Lyase—Purification, Properties, and Identification of Catalytically Essential Dehydroalanine," *J Biol Chem*, 246(9):2977-85 (1971).

Hofstetter, et al., "Antibodies as chiral selectors for the determination of enantioenrichment," *Enantiomer*, 6:153-158 (2001).

Horton et al., "Interference patterns of a plane-polarized wave from a hollow glass fiber," *J Opt Soc Am*, 63:1204-1210 (1973).

Hubbard et al., "Calmodulin binding by calcineurin," *J Biol Chem* 262(31):15062-15070 (1987).

Huntley, "Speckle photography fringe analysis: assessment of current algorithms," *Applied Optics*, vol. 28:4316 (1989).

Jacobson, et al., "Fused Quartz Substrates for Microchip Electrophoresis," *Anal Chem*, 67:2059-2063 (1995).

Jacobson, et al., "Microfluidic devices for electrokinetically driven parallel and serial mixing," *Anal Chem*, 71:4455-4459 (1999).

Kalghatgi, et al., "Microbial L-phenylalanine ammonia-lyase. Purification, subunit structure and kinetic properties of the enzyme from *Rhizoctonia solani*," *Biochem J*, 149:65-75 (1975).

Kalinina, et al., "Nanoliter scale PCR with TaqMan detection," *Nucleic Acid Research*, 25(10):1999-2004 (1997).

Kerker, et al., "Scattering of Electromagnetic Waves from Concentric Infinite Cylinders," *J Opt Soc Am*, 51:506-508 (1961).

Klee et al., "Purification of cyclic 3',5'-nucleotide phosphodiesterase inhibitory protein by affinity chromatography on activator protein couples to sepharose," *Biochem* 17:120-126 (1978).

Korbel, et al., "Reaction microarrays: A method for rapidly determining the enantiomeric excess of thousands of samples,"*J Am Chem Soc*, 123(2):361-362 (2001).

Kuhlmann, "Drug Research: From the Idea to the Product," Int J Clin Pharmacol Ther, 35(12):541-552 (1997).

Lan et al., "Non-mechanical sub-pixel image shifter for acquiring super-resolution digital images," *Optics Express*, vol. 17:22992-23002 (2009).

Langone, "Protein A of *Staphylococcus aureus* and related immunoglobulin receptors produced by *Streptococci* and *Pneumonococci*," *Adv Immunol*, 32:157-252 (1982).

Latham et al., "Photobiotin surface chemistry improves label-free interferometric sensing of biochemical interactions," *Angew Chem Int Ed*, 45:955-958 (2006).

Liu, et al., "Optimization of high-speed DNA sequencing on microfabricated capillary electrophoresis channels," *Anal Chem*, 71:566-573 (1999).

Manz, et al., "Micromachining of Monocrystalline Silicon and Glass for Chemical-Analysis Systems—a Look into Next Century Technology or Just a Fashionable Craze?," *Trac-Trends in Anal Chem*, 10(5):144-149 (1991).

Manz, et al., "Miniaturized Total Chemical-Analysis Systems—a Novel Concept for Chemical Sensing," *Sensors and Actuators B:Chemical*, 1:244-248 (1990).

Marcuse et al., "Light scattering from optical fibers with arbitrary refractive-index distributions," *J Opt Soc Am*, 65:367-375 (1975).

Markov, et al., "Breaking the 10-7 Barrier for RI Measurements in Nanoliter Volumes," Anal Chem, 74:5438-5441 (2002).

Markov et al., "A fourier analysis approach for capillary polarimetry," *Electrophoresis*, 23:809-812 (2002).

Markov et al., "Label-Free Molecular Interaction Determinations with Nanoscale Interferometry," *J Am Chem Soc* 126:16659-16664 (2004).

Markov, et al., "Non-Invasive Fluid Flow Measurements in Microfluidic Channels with Backscatter Interferometry," *Electrophoresis*, 25(21-22):3805-3809 (2004).

Martynova, et al., "Fabrication of plastic microfluid channels by imprinting methods," *Anal Chem*, 69:4783-4789 (1997).

May, et al., "Inverting enantioselectivity by directed evolution of hydantoinase for improved production of L-methionine," *Nat Biotech*, 18(3):317-320 (2000).

Maystre, et al., "Enhanced Polarimetric Detection in Hplc Using a Refractive-Index Index Equalizer," *Anal Chem*, 66:2882-2887 (1994).

Miroshnikova et al., "Percussion hole drilling of metals with a fourth-harmonic Nd:YAG laser studied by defocused laser speckle correlation," Applied Optics, vol. 44:3403 (2005).

Montigiani et al., "Alanine substitutions on calmodulin-binding peptides result in unexpected affinity enhancement," *J Mol Biol* 258:6-13 (1996).

Morrison, et al., "Nanoliter high throughput quantitative PCR," *Nucleic Acid Res*, 34(18):e123 (2004).

Neifeld, "Information, resolution, and space—bandwidth product," Optics Letters, vol. 23:1477-1479 (1998).

Pitter et al., "Focus errors and their correction in microscopic deformation analysis using correlation," Optics Express, vol. 10:1361-1367 (2002).

Quake, et al., "From micro- to nanofabrication with soft materials," *Science*, 290:1536-1540 (2000).

Read, et al., "Aseptic meningitis and encephalitis: the role of PCR in the diagnostic laboratory," *Clin Microbiol*, 35:691-696 (1997).

Reem et al, "Induction and upregulation by interleukin 2 of high-affinity interleukin 2 receptors on thymocytes and T cells," *Proc Natl Acad Sci USA*, 82:8663-8666 (1985).

Reetz, "Combinatorial and evolution-based methods in the creation of enantioselective catalysts," *Angew Chem Int Ed*, 40:284-310 (2001).

Reetz, "New methods for the high-throughput screening of enantioselective catalysts and biocatalysts," *Angew Chem Int Ed*, 41:1335-1338 (2002).

Resetar, et al., "Anticipating Technological Change: Combinatorial Chemistry and the Environment," *EPA*, 2001.

Rich et al., "High-resolution and high-throughput protocols for measuring drug/human serum albumin interactions using BIACORE," *Anal Biochem* 296:197-207 (2001).

Rother, et al., "An active site homology model of phenylalanine ammonia-lyase from *Petroselinum crispum*," *Eu J Biochem*, 269:3065-3075 (2002).

Rouhi, "Chiral chemistry," *Chem Eng News*, 82(24):47-62 (2004).

Rouhi, "Chiral roundup—As pharmaceutical companies face bleak prospects, their suppliers diligently tend the fertile fields of chiral chemistry in varied ways," *Chem Eng News*, 80(23):43-50 (2002).

Rouhi, "Chiral roundup—Taking a measure of chiral riches—Researchers respond to high demand for ways to measure enantioenrichment quickly," *Chem Eng News*, 80(23):51-57 (2002).

www.rudolphresearch.com/polarimetry.htm, (last accessed Aug. 3, 2009).

Saha et al., "Comparative study of IgG binding to proteins G and A: Nonequilibrium kinetic and binding constant determination with the acoustic waveguide device," *Anal Chem*, 75:835-842 (2003).

Schonfeld, et al., "Polarimetric assay for the medium-throughput determination of alpha-amino acid racemase activity," *Anal Chem*, 76:1184-1188 (2004).

Schuster, et al., "The Mechanism of Action of Phenylalanine Ammonia-Lyase—the Role of Prosthetic Dehydroalanine," *Proc Natl Acad Sci USA*, 92(18):8433-8437 (1995).

Sidick et al., "Adaptive cross-correlation algorithm for extended scene Shack—Hartmann wavefront sensing," Optics Letters, vol. 33:213-215 (2008).

Sjodahl, "Accuracy in electronic speckle photography," Applied Optics, vol. 36:2875-2885 (1997).

Sjodahl et al., "Electronic speckle photography: analysis of an algorithm giving the displacement with subpixel accuracy," Applied Optics, vol. 32:2278-2284 (1993).

Sjodahl, "Electronic speckle photography: increased accuracy by nonintegral pixel shifting," Applied Optics, vol. 33:6667-6673 (1994).

Sjodahl et al., "Measurement of shape by using projected random patterns and temporal digital speckle photography," Applied Optics, vol. 38:1990-1997 (1999).

Soumet, et al., "Identification by a multiplex PCR-based assay of *Salmonella typhimurium* and *Salmonella enteritidis* strains from environmental swabs of poultry houses," *Lett Appl Microbiol*, 29(1) 1-6 (1999).

Sorensen, et al. "Absolute refractive index determination by microinterferometric backscatter detection," *Anal Chem*, 75:1946-1953 (2003).

Speaker, et al., "Characterization of a calmodulin-binding protein that is deficient in trifluoperazine-resistant variants of the macrophage-like cell line J774," *Proc Natl Acad Sci USA*, 80:329-333 (1983).

Svanbro et al., "Complex amplitude correlation for compensation of large in-plane motion in digital speckle pattern interferometry," Applied Optics, vol. 45:8641-8647 (2006).

Swinney, et al., "Capillary-scale polarimetry for flowing streams," *Analyst*, 126:673-675 (2001).

Swinney, et al., "Chip-scale universal detection based on backscatter interferometry," *Anal Chem*, 72:2690-2695 (2000).

Swinney, et al., "A chip-scale universal detector for electrophoresis based on backscattering Interferometry," *Analyst*, 125:1713-1717 (2000).

Swinney, et al., "D-beta-Hydroxybutyrate reaction kinetics studied in nanoliter volumes using a capillary polarimeter," *Applied Spectroscopy* 54:1485-1489 (2000).

Swinney, et al., "Laser-Based Capillary Polarimetry," *J Capill Electrophor Microchip Technol*, 6(3-4):93-96 (1999).

Swinney, et al., "Micro-interferometric backscatter detection using a diode laser," *Analytica Chimica Acta*, 400:265-280 (1999).

Swinney, et al., "Nanoliter volume polarimetry," *Applied Spectroscopy*, 56:134-138 (2002).

Swinney, et al., "Noninvasive picoliter volume thermometry based on backscatter Interferometry," *Electrophoresis*, 22(1):2032-2036 (2001).

Swinney, et al., "Quantification and evaluation of Joule heating in on-chip capillary electrophoresis," *Electrophoresis*, 23(4):613-620 (2002).

Swinney, et al., "Ultrasmall volume refractive index detection using microinterferometry," *Rev Sci Instrum* 71:2684-2692 (2000).

Synnergren et al., "Application of digital speckle photography to flash x-ray studies of internal deformation fields in impact experiments," Applied Optics, vol. 36:4030-4036 (1999).

Synnergren et al., "Digital speckle photography: visualization of mesoflow through clustered fiber networks," Applied Optics, vol. 41:1368-1373 (2002).

Synnergren et al. "Optical in-plane strain field sensor," Applied Optics, vol. 41:1323-1329 (2002).

Takushima et al., "Optical reflectometry based on correlation detection and its application to the in-service monitoring of WDM passive optical network," Optics Express, vol. 15:5318-5326 (2007).

Tan, et al., "Rapid fabrication of microfluidic devices in poly(dimethylsiloxane) by photocopying," *Lab on a Chip*, 1:7-9 (2001).

Tarigan et al., "Capillary-scale refractive index detection by interferometric backscatter," *Anal Chem*, 68:1762-1770 (1996).

Theze, et al., "Interleukin 2 and its receptors: recent advances and new immunological functions," *Immunology Today* 17:481-486 (1996).

Török, "Calmodulin conformational changes in the activation of protein kinases," *Biochem Soc Trans* 30:55-61 (2002).

Tsukamoto, et al., "Recent advances in the measurement of enantiomeric excesses," Advanced Synthesis & Catalysis 344:453-463 (2002).

van Delden, et al., "Color indicators of molecular chirality based on doped liquid crystals," *Angew Chem Int Ed*, 40:3198-3200 (2001).

Viola et al., "Alignment by maximization of mutual information", International Conference on Computer Vision (E. Grimson, S. Shafer, A. Blake and K. Sugihara, eds.), IEEE Computer Society Press, Los Alamitos, CA, pp. 16-23, 1995.

Vogelstein, et al., "Digital PCR," *Proc Natl Acad Sci USA*, 96(16):9236-9241 (1999).

Wang, et al., "High-speed digital-image correlation method," Optics Letters, vol. 34:1955-1957 (2009).

Wang et al.,"Optical vortex metrology for nanometric speckle displacement measurement," Optics Express, vol. 14:120-127 (2006).

Wang et al., "Pseudophase information from the complex analytic signal of speckle fields and its applications. Part I: Microdisplacement observation based on phase-only correlation in the signal domain," Applied Optics, vol. 44:4909-4915 (2005).

Watkins, "Scattering from side-illuminated clad glass fibers for determination of fiber parameters," *J Opt Soc Am*, 64:767-772 (1974).

Whitesides et al., "Soft lithography in biology and biochemistry," *Annu Rev Biomed Eng*, 3:335-373 (2001).

Wu, et al. "Polymer microchips bonded by 0-2-plasma activation," *Electrophoresis*, 23:782-790 (2002).

Yamaguchi, "Fringe formation in speckle photography," J. Opt. Soc. Am. A, vol. 1:81-86 (1984).

Yanik, et al., Development of a New Laser Based Polarimetric Detector and Its Application to High-performance Liquid Chromatography. PDR-Chiral, 1998.

Yeung, et al., "Electrochemistry-Based Real-Time PCR on a Microchip," *Anal Chem*, 80:363-368 (2008).

Young, et al., "Novel Recombinant-Antigen Enzyme Immunoassay for Serological Diagnosis of Syphilis," *J Clin Microbio*, 36(4):913-917 (1998).

Yu et al., "Energy landscape of aptamer/protein complexes studies by single-molecule force spectroscopy," *Chem Asian J*, 2:284-289 (2007).

Zandonella, "Cell nanotechnology: The tiny toolkit," *Nature*, 423:10-12 (2003).

Zhihong et al., "A new sandwich-type assay of estrogen using piezoelectric biosensor immobilized with estrogen response element," *Anal Commun*, 36:281-283 (1999).

PCT/US2008/063879, May 16 2008, Jones, Written Opinion, Aug. 19, 2008.

PCT/US2008/063879, May 16, 2008, Jones, International Search Report, Aug. 19, 2008.

PCT/US2008/063879, May 16, 2008, Jones, International Preliminary Report on Patentability, Nov. 24, 2009.

U.S. Appl. No. 12/122,715, filed May 16, 2008, Jones, Non-Final Office Action, Apr. 28, 2010.

U.S. Appl. No. 12/122,715, filed May 16, 2008, Jones, Response to Non-Final Office Action, Jun. 29, 2010.

U.S. Appl. No. 12/122,715, May 16, 2008, Jones, Notice of Allowance, Jul. 22, 2010.

PCT/US2005/38168, Oct. 22, 2004, Bornhop, Written Opinion, Apr. 26, 2006.

PCT/US2005/38168, Oct. 22, 2004, Bornhop, International Search Report, Apr. 26, 2006.

PCT/US2005/38168, Oct. 22, 2004, Bornhop, International Preliminary Report on Patentability, Apr. 27, 2007.

PCT/US2008/077145, Sep. 20, 2008, Bornhop, Written Opinion, Dec. 8, 2008.

PCT/US2005/077145, Sep. 20, 2008, Bornhop, International Search Report, Dec. 8, 2008.

PCT/US2008/077145, Sep. 20, 2008, Bornhop, International Preliminary Report on Patentability, Mar. 24, 2010.

\* cited by examiner

ON-CHIP POLARIMETRY FOR HIGH-THROUGHPUT SCREENING OF NANOLITER AND SMALLER SAMPLE VOLUMES

CROSS REFERENCE TO RELATED APPLICATIONS

This application claims the benefit, under 35 U.S.C. 119 (e), of U.S. Provisional Application No. 60/620,661, which was filed on Oct. 22, 2004 and is hereby incorporated by reference.

ACKNOWLEDGEMENT

This invention was made in the course of research partially supported by a grant from the National Aeronautics and Space Administration (NASA), Grant No. NNC04AA52A. The United States government has certain rights in the invention.

BACKGROUND OF THE INVENTION

1. Field of the Invention

The present invention relates to a biological reaction analysis technique that employs an on-chip polarimeter (OCP) to monitor optical activity in samples contained in one or more microfluidic channels formed in a chip or substrate. The sample in each channel is illuminated by a linearly polarized laser beam and the resulting interference fringe pattern in the light scattered by the sample is interrogated with a transducer. The technique is particularly suited for high-throughput analysis.

2. Description of the Background Art

The ability to measure optical activity is essential in the pharmaceutical, food and biotechnology industries. It is particularly important in the development of new drugs, with the vast majority of medicines and drug metabolites being chiral and with the worldwide sale of chiral drugs in single-enantiomer dosages exceeding $147 billion in 2001. Chiral molecules, which exist in pairs of optical isomers called enantiomers that are structurally identical, with the same physical properties, and differ only in their three-dimensional spatial arrangement. In effect, the two enantiomers are just like a pair of hands in that they are non-superimposable mirror images of one another with no planes of symmetry. In the industries, the two isomers are referred to as R and S isomers.

Drugs work by reacting with receptors in the body that have a specific physical shape and usually fit one enantiomer better than the other. In other words, one isomer binds preferentially while the other has little or no activity. While there are examples where both enantiomers have similar therapeutic properties, there are many other cases where one of the isomers causes serious side-effects. As a result, all chiral forms of a drug now have to be tested rigorously for possible side-effects and for chiral stability in vivo before approval. The FDA insists on switching to the pure enantiomer for older drugs and will only approve single isomers of new chiral drugs. It is therefore certain that the percentage of single-enantiomer dosages will grow from the current level of 40% of all drug sales.

With the advent of combinatorial chemical methods and the implementation of parallel synthesis coupled with high-throughput screening, the pace of research in drug discovery has significantly accelerated. A significant number of chiral drug precursors are now produced by enzyme catalyzed processes. Improvements in enzyme specificity and activity are now increasingly being obtained via "directed evolution" methodologies. One of the main challenges of combinatorial asymmetric catalysis and directed evolution is the requirement to screen libraries ranging from $10^4$ to $10^7$ members. Recent reports further demonstrate the importance of producing and analyzing chiral compounds. Several reviews have been provided on the advances in the methodologies for the determination of enantiomeric excesses, noting the significant analytical challenges of all things combinatorial.

While no technique is ideal, progress has been made toward the high-throughput (HT) screening of enantioselective enzymes and biological processes, for the purpose of directed evolution. The most obvious approach, UV/Vis, has been restricted to the hydrolytic kinetic resolution of chiral p-nitrophenol esters catalyzed by lipases or esterases (4,800 samples/day, 9% precision). Fluorescence assays require an active probe attached to the substrate (8,000 samples/day, 10% precision). NMR requires pseudo-enantiomers to be created (1,400 samples/day, 5% precision). Capillary array electrophoresis requires a fluorescence-active reagent (20,000 samples/day, 3% precision) and employs the somewhat tedious CE separation technique. Gas chromatography can provide exact ee determinations but is complicated and limited to volatile compounds with throughput of 700 measurements per day. Circular dichrosim (CD) can also provide exact ee determinations but is limited to 700-900 measurement/day and requires complicated calculations. MS requires a mass-tagged chiral derivatization (be rendered "pseudo-enantiomeric" so the enantiomers differ in mass) agent be applied to the mixture (10,000 samples/day, 2% uncertainty). Among the more fascinating techniques for HT ee determinations, include a color test using chirality-dependent doped films of liquid crystals, fluorescent reporting using a DNA microarray, an assay employing antibodies that is an analog of competitive enzyme immunoassay and a technique termed EMDee which is an enzymatic method for determining enantiomeric excess. These promising techniques are somewhat limited by moderate throughput, the need for sample labeling or large amounts of sample.

Polarimetry, an intrinsic optical technique, can provide a quantitative measure of optical activity or chirality. If a plane of polarized light is passed through a sample of each enantiomer in a pair, one will rotate the polarization of the light to the left (levorotatory or (−)-enantiomer), and the other will rotate the polarization plane to the right (dextrorotatory or (+)-enantiomer). This response is proportional to concentration of the chiral molecule, it can be very sensitive, and is a nondestructive well-established technique. For these reasons a number of groups have worked towards improving the performance of the polarimeter for measuring optical activity while reducing the sample size needed for an assay.

One polarimetry device known as a capillary polarimetric detector (CPD) was developed in 1996 that demonstrated for the first time that polarimetric measurements could detect changes in optical activity at the micromolar level in nanoliter volumes and that these measurements had little sensitivity to refractive index perturbations. The CPD has a simple optical train based on a 4-mW polarized He/Ne laser, a polarizing plate with an extinction ratio of 1:10,000 to further purify the polarization state of the beam, a fused silica capillary tube containing the sample to be analyzed and a transducer for receiving the fringe patterns that are caused by interaction of the laser light with the sample in the capillary. Using the CPD it appears possible to quantify rotation at the level of $9 \times 10^{-6}$°. The device has been used to analyze D-β-hydroxybutyrate at the picomole level, for the determination of absolute optical activity and very recently for flowing stream analysis. However, the CPD is not a high-throughput device, nor is it inherently compatible with microfluidics technology. Microfluidics allows higher order system integration and ease in sample multiplexing resulting reduced sample consumption and analysis time. To fully realize the potential of microfluidics, detectors that directly interrogate the sample in the channel on the chip, without loss in sensitivity must be developed.

There appear to be two fundamental limitations in the implementation of all previous approaches based on conventional polarimetry for HT measurements or for use as an on-chip optical activity detector; first they demand very high extinction ratios (possible with Glan-Thompson prisms, but problematic for imaging systems due to a limited NA) so as to measure small optical rotation changes. The most common approach used in HT screening is to illuminate a multiwell plate and use an imaging system to collect the light from all of the samples in the well plate simultaneously. Second, conventional polarimeters have an inherent path length dependency as defined by Biot's law and thus have poor sensitivity for optical activity in the short path lengths of a multiwell plate.

SUMMARY OF THE INVENTION

The present invention is directed to a polarimetry technique for measuring optical activity that is particularly suitable for HT screening. The technique employs a chip or substrate having one or more microfluidic channels formed therein of micron dimensions. In the technique, referred to as "on-chip polarimetry" (OCP), a polarized laser beam is directed onto fluid samples of optically active molecules that are disposed in the channels in the chip. The incident laser beam interacts with the molecules, which causes a slight rotation of the polarization of the light beam in one direction or another, depending on the nature of the molecules in the sample. The sample molecules and the channel walls interact with the laser beam and result in generation of interference fringe patterns that radiate from the channels in multiple directions. A suitable detector, such as a CCD, is positioned to receive the interference fringe patterns. In one embodiment, the detected fringe patterns radiate in a direction that is almost parallel to the incident laser beam such that the received fringe patterns are scattered back toward the detector by the sample. In another embodiment referred to as side scatter OCP (SOCP), the detector receives radiation that is scattered at an angle approaching 90 degrees from the axis of the incident laser beam, in which case the detector receives radiation that is scattered off to one side of the channel.

In the direct backscatter embodiment, the microfluidic chip provides optical interfaces (air to chip substrate, substrate to sample solution contained in the channel, and sample solution to back of chip). The incoming beam is split and reflected at each optical interface and rays pass multiple times through the sample solution contained within the channel, leading to an unexpected sensitivity gain over single pass configurations. The fringe pattern is created by the constructive and destructive interference caused by beams that reflect from the surface of the chip and those that pass through the solution.

In this embodiment, a polarizer plate is positioned between the sample channel and the detector that acts as an analyzer plate by allowing a selective amount or light to pass through, the intensity of which is proportional to a degree by which optically active molecules in the sample rotate the polarization plane of the laser beam as it passes through the sample. The analyzer polarizer plate eliminates low frequency refractive index based variations in the detected fringe patterns that would interfere with the ability to detect the polarization related variations in the signals. This configuration functions like a conventional polarimeter, yet with a unique S/N enhancement due to the laser-channel interaction.

An evaluation of the OCP interference pattern unexpectedly revealed that the side scatter on-chip polarimeter (SOCP) embodiment can be used without a second polarizer (analyzer plate), greatly simplifying the optical train and further enabling HT polarimetry configurations.

In both embodiments, the amount by which incident light is rotated one way or the other by the sample is an indication of the relative concentration of a particular isomer in the sample, for example. Since the intensity of the detected scattered radiation varies in portion to the amount of polarization rotation, the intensity can be employed to measure the concentration level in the sample. The system can therefore be employed to determine what types of molecules are present in a sample or to determine the concentration level of molecules in the sample.

The chip in which the one or more channels are formed can be made of any suitable material, but is preferably made from either glass (e.g. fused silica) or a plastic material, such as PDMS (polydimethylsiloxane). In the case of fused silica, the channels are preferably etched into the silica such that the resulting cross sections of the channels are generally hemispherical in shape. In a variation using a PDMS chip, it is easier to form the channels with a rectangular cross section. In either case, a multipass arrangement is created in which the incoming laser beam is reflected by the channel walls so that the beam passes through the sample multiple times before it exits the sample and is incident on the photodetector. As a result, each time the beam passes through the sample, the optically active molecules therein will cause incremental rotation of the polarization plane, which increases sensitivity of the system.

In a high-throughput (HT) embodiment of the invention that can be employed to perform multiple analyses on a single chip, a multichannel plate is employed along with a moving carriage that is capable of accurate placement in two dimensions. The laser beam is fed through an optical fiber that terminates in a collection of optics mounted on the movable carriage. A collection fiber optic or a photodetector is also mounted on the carriage. The carriage is positioned in the x and y directions using a high precision motorized translation system that allows exact placement of the laser beam over each channel to create the interference pattern for each sample in each channel that is then sensed with the detector.

BRIEF DESCRIPTION OF THE DRAWINGS

The features and advantages of the present invention will become apparent from the following detailed description of a number of preferred embodiments thereof, taken in conjunction with the following drawings, in which.

DETAILED DESCRIPTION OF THE PREFERRED EMBODIMENTS

Figure 1:
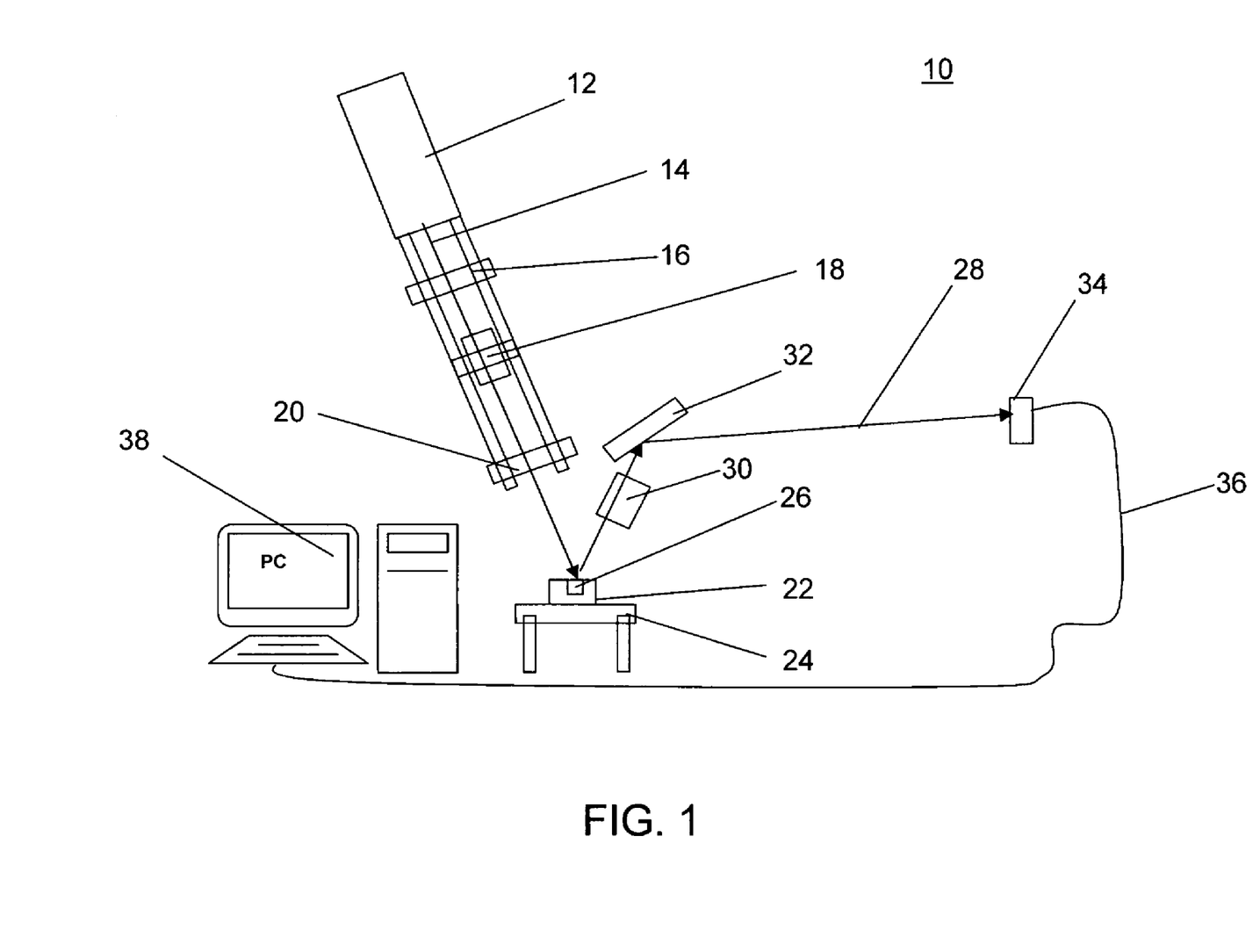
FIG. 1 is a schematic illustration of a system constructed in accordance with first and second preferred embodiment of the present invention for conducting on-chip polarimetry measurements of a fluid sample contained in a channel in a chip or substrate.

With reference to FIG. 1, an OCP system 10 is illustrated that can be configured for direct backscatter or side scatter measurements in accordance with first and second preferred embodiments of the present invention. The OCP system 10 is comprised of a light source 12, such as a helium neon (HeNe) laser, which generates a coherent polarized laser beam 14. The laser beam 14 is first directed through an optional neutral density filter or attenuator 16, which reduces the intensity of the beam 14, and then through a first Glan-Thompson (GT) polarizer 18 that further purifies the polarization of the beam 14 for maximizing measurement sensitivity of the system 10. A typical HeNe laser generates a polarized beam with a 600:1 extinction ratio (the ratio of rays with one polarization state to those of the opposite polarization state). In contrast, the GT polarizer 18 increases the extinction ratio to on the order of 100,000:1, which results in the laser beam 14 being virtually purely plane polarized. The laser beam 14 next passes through a half wave plate 20 to allow the plane of polarization of the beam to be rotated as desired. The beam 14 is then incident on a chip 22 mounted on an aluminum black anodized block 24, which preferably includes a Peltier cooler controlled by a high precision temperature controller (not shown) to minimize temperature perturbations.

The incident laser beam 14 interacts with a sample contained in an elongated channel 26 (best shown in FIGS. 3A and 3B) that is formed in the chip 22. As the beam interacts with the microfluidic channel 26, some of the rays reflect off the surface and some of the rays enter the channel 26 and interact with the fluid sample therein. The rays that enter the channel 26 become trapped, reflecting off of the walls of the channel 26 and making multiple passes through the sample. This allows a ray to interact with the sample molecules multiple times. The rays escape and combine with those that reflected off the surface of the channel 26. This produces an interference fringe pattern (series of bright and dark spots) 28.

In the backscatter embodiment, the interference fringe pattern 28 is directed through a second GT polarizer 30. The second GT polarizer 30 acts the same as an analyzer in a conventional polarization detection system by allowing radiation to pass through only if the polarization of the fringe pattern 28 is rotated relative to the plane of polarization in the incident laser beam 14. In the backscatter embodiment, the second GT polarizer 30 is necessary because the interference fringe pattern 28 does not contain any high frequency fringes that are related to polarization, but instead is dominated by low frequency refractive index related fringes. As will be discussed further later, this second, analyzer polarizer 30 is not needed to perform relative optical activity determinations in a second embodiment that employs detection of side scattered radiation.

A section of the fringe pattern (the first three fringes adjacent to the centroid) is passed through the second GT polarizer 30 and is then reflected off of an optional mirror 32 onto a charge-coupled device (CCD) 34 or other suitable photodetector. The CCD 34 generates an electrical output signal that is fed through a cable 36 as input to a computer 38 or other suitable analyzer for storage and polarization analysis to determine some characteristic of the sample that affects the polarization orientation of the beam as it interacts with the sample. These three elements thus combine to form a polarization detector.

Figure 2A:
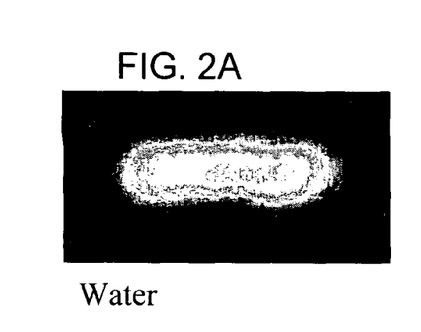
FIGS. 2A-2F are images and graphs showing the interference fringe patterns and intensities that were obtained with the system of FIG. 1 in experiments on water and a known optically active material, mandelic acid.
Figure 2B:
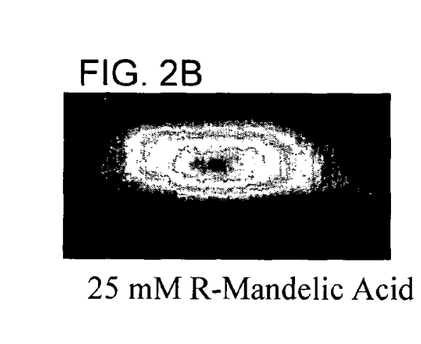
Figure 2C:
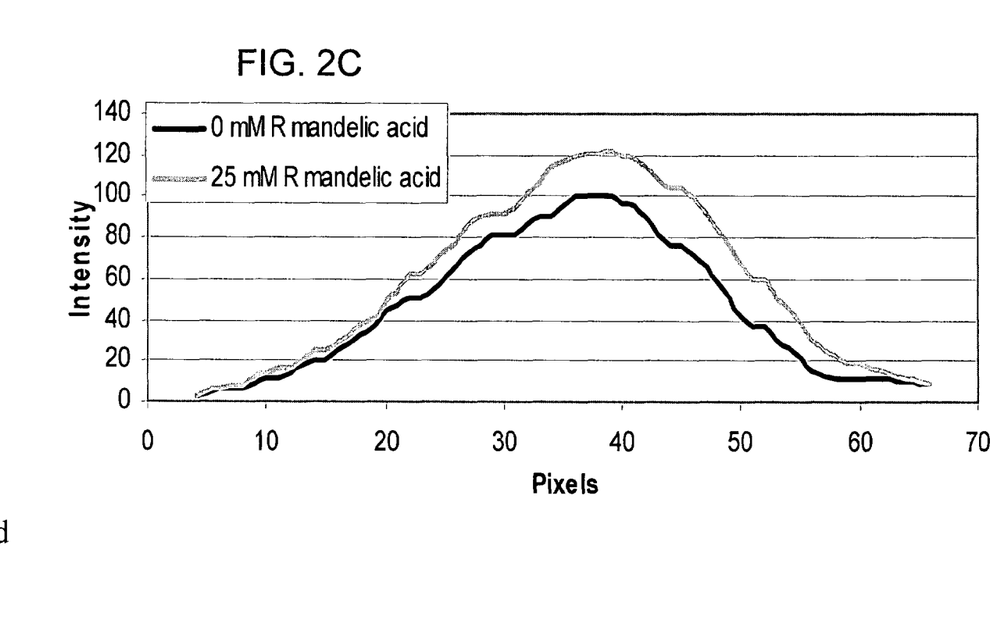

FIGS. 2A-2C illustrate actual fringe patterns (false color image obtained by a laser beam analyzer) and an intensity profile of a cross-section of these fringes that were obtained during experiments on the system 10 of FIG. 1 using water and mandelic acid. Since this embodiment of the system 10 uses a two-polarizer configuration, the polarimetric signal is encoded in the intensity of the fringe pattern and can give absolute optical activity values for the unknown sample.

Figure 2D:
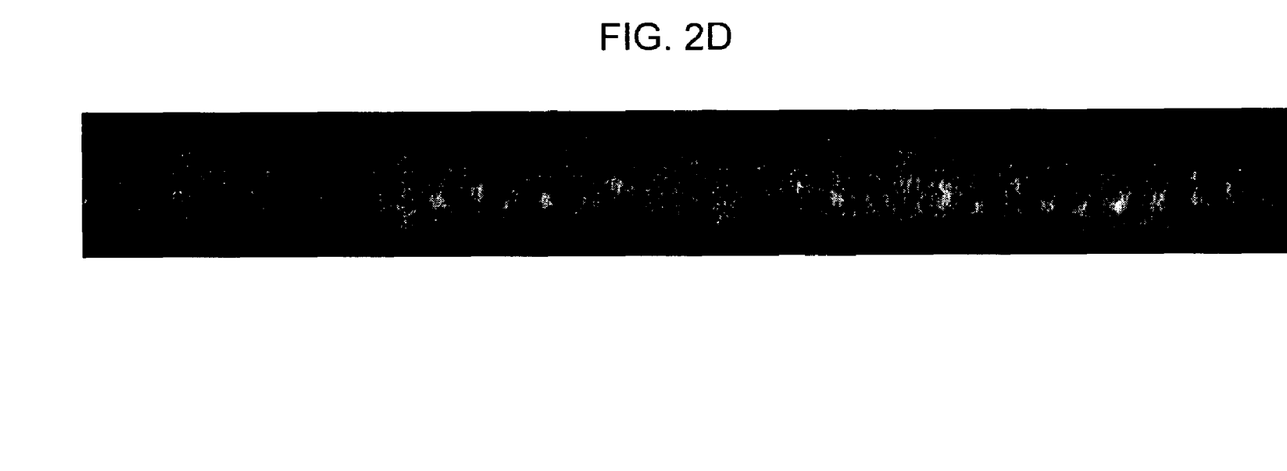
Figure 2E:
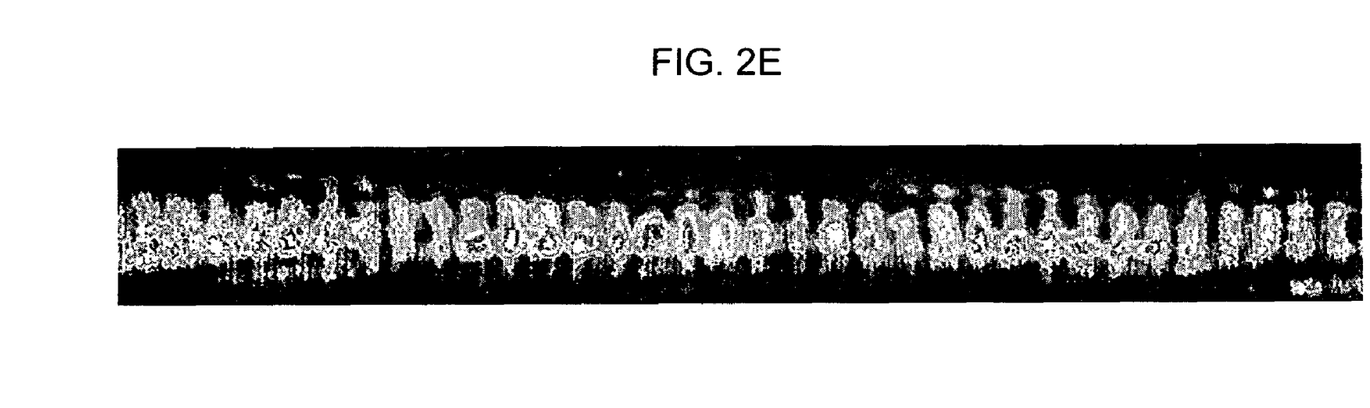
Figure 2F:
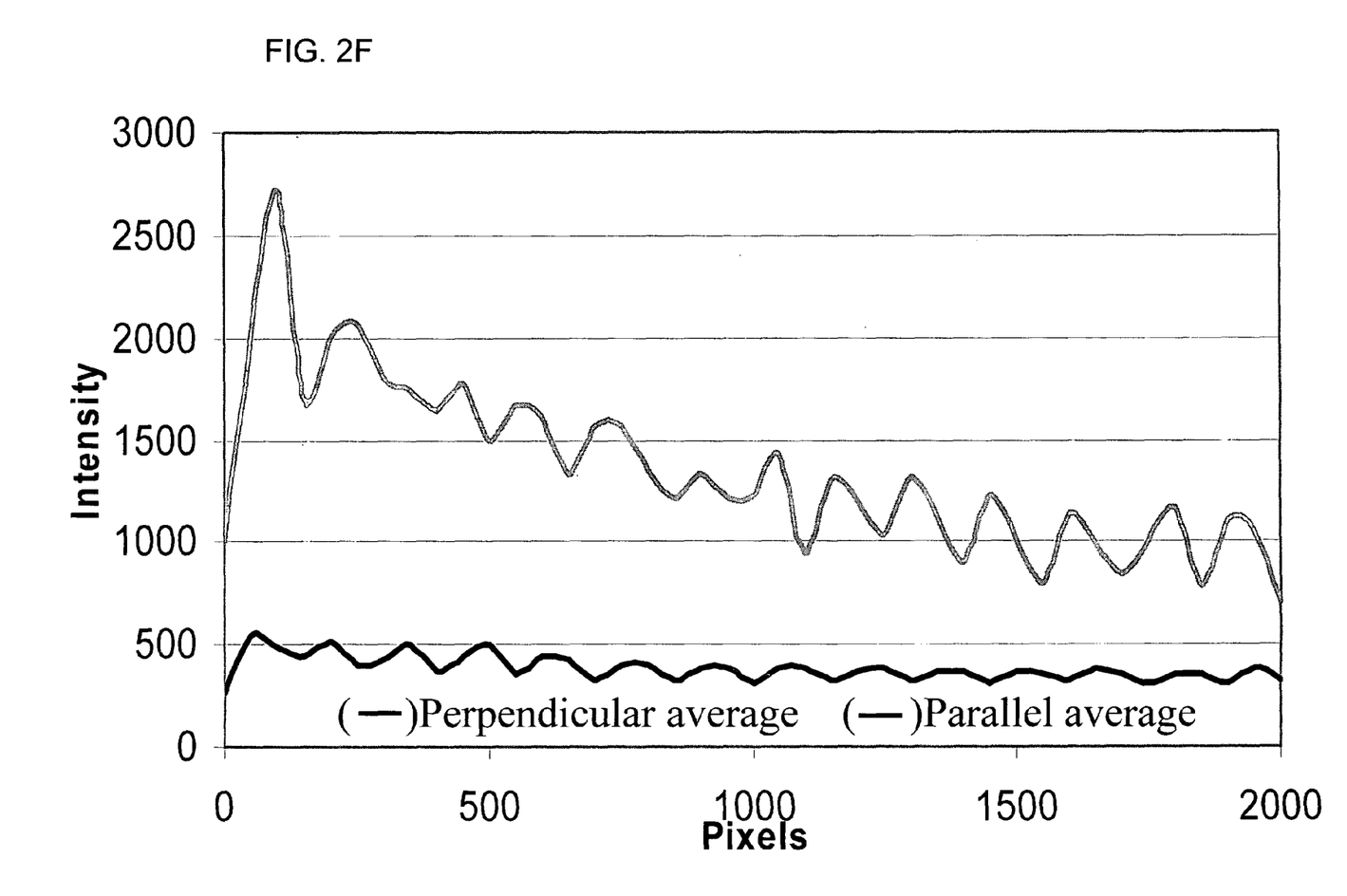

FIGS. 2D (minimum half wave plate position) and 2E (maximum half wave plate position) are false color images of the side scatter fringes obtained by a laser beam analyzer. FIG. 2F is a graph of an average intensity of a cross section of the two patterns.

Figure 3A:
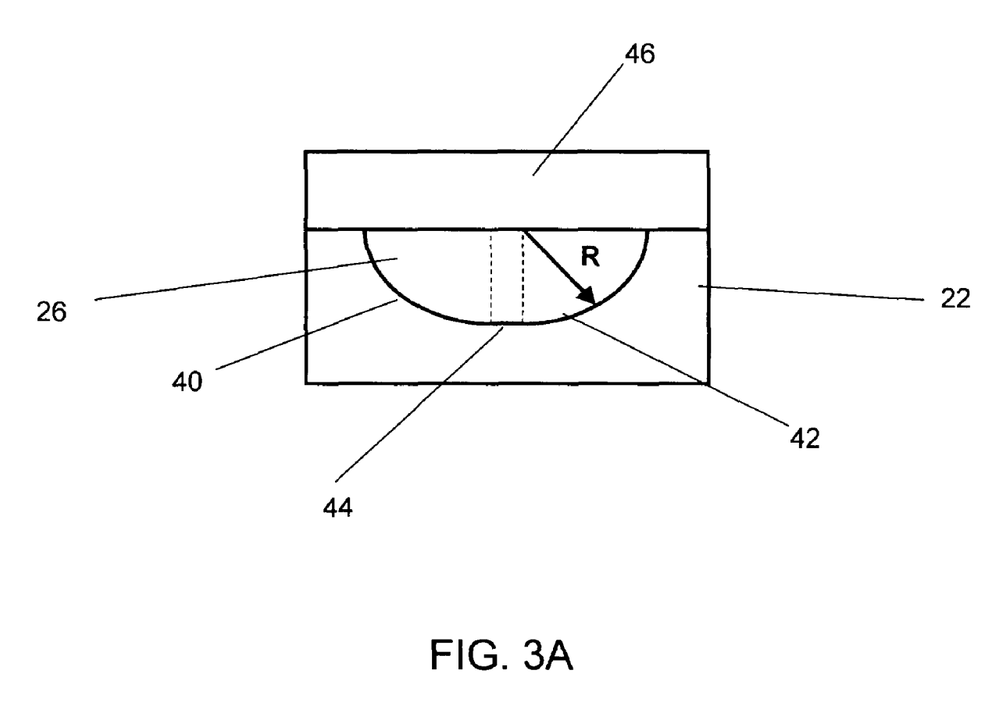
FIGS. 3A and 3B are schematic illustrations of the cross sections of a channel formed in a chip for use in a first variation of the first preferred embodiment in which a silica chip is employed, and for use in a second variation of the first preferred embodiment in which a plastic chip is employed, respectively.
Figure 3B:
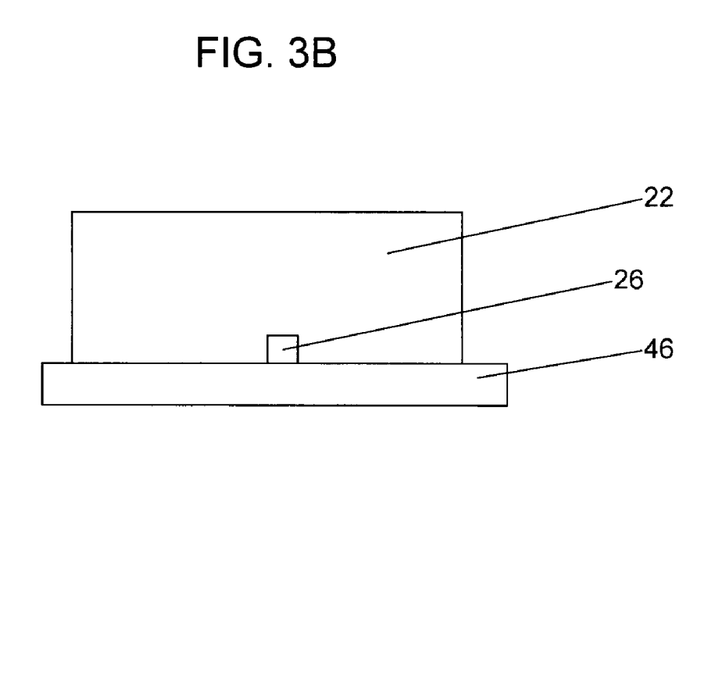

The cross sections of two different variations of the chip 22 are illustrated in FIGS. 3A and 3B, respectively. In FIG. 3A, the chip 22 is preferably formed from glass, such as fused silica, and includes a generally hemispherical shaped channel 26 that is isotropically etched, molded or otherwise formed in the chip 22. In the embodiment in FIG. 3A, the channel 26 includes first and second curved sections 40 and 42 each of 40 μm radius R and a 10 μm flat section 44 that separates the curved sections. The flat section 44 is not necessary but is present in the preferred embodiment because of the isotropic etching technique that is employed to make the first and second curved sections one at a time. A transparent cover plate 46 is placed on top of the chip 22 to seal the channel 26.

In the variation illustrated in FIG. 3B, the chip 22 is preferably made of an optical quality plastic material, such as polydimethylsiloxane (PDMS). In this variation, the PDMS 22 is formed using photolithographic techniques to create a desired channel. Then the PDMS and a glass slide are oxidized. The channel is formed with three walls from the PDMS and the back is from the glass slide. In this instance, the channel 26 is rectangular in shape because this shape is easier to form in PDMS, or to mold into optical quality plastics.

In either variation, experiments and theoretical models have shown that the incident laser beam 14 is reflected off of the channel walls many times before it exits the channel. As a result, the beam makes multiple passes through the sample in the channel 26, which enhances sensitivity because the optically active material in the sample incrementally alters the polarization of the beam on each pass. In an experiment, the system 10 was found to have excellent sensitivity to changes in optical activity, even in 50-90 μm wide microfluidic channels. Employing an HeNe laser with a beam diameter of ca. 0.6 mm yields a polarimeter with a 1.8 nL probe volume.

To demonstrate that the OCP 10 performs as a polarimeter, Malus Law response was evaluated. Malus Law describes the relationship between the light intensity (I) and the angle of the principal plane of polarization of the illumination source ($I_0$) with respect to the analyzer plate, equation 1.

$$I = I_0 \times \cos^2(\theta) \qquad \text{Eq. (1)}$$

This test was done by measuring the intensity output (sensitivity of the system) as a function of polarization state of the incoming beam. With water in the microfluidic channel 26, the half-wave plate 20 was rotated to impart a change in polarization plane of the laser beam 14 with respect to the channel 26. Intensity measurements were taken every five degrees and the intensity of the fringe pattern vs. half-wave plate angle was plotted. An $R^2$ value of 0.999 was obtained when fitting the OCP response to a $\cos^2$ fit, thus indicating excellent correlation and confirming that the system obeys Malus Law.

A test of the embodiment of FIG. 1 was then conducted to verify that the system 10 can be employed to quantify optical activity in a sample contained in the microfluidic channel 26. It was determined first that by positioning the half-wave plate 20 at approximately 134° relative to the minimum intensity, a large change in intensity vs. solute induced rotation could be quantified. Such a configuration allows the determination of whether the OCP system 10 can be used to discriminate between R and S isomers using the increase or decrease of intensity caused by rotation of the plane of polarization in opposite directions by each isomer. Glycerol solutions were used to demonstrate that the OCP system 10 is insensitive to large RI changes. To test the response of the system 10 to optically active solutions, R- and S-mandelic acid, $[\alpha]^{25}=+154°$ and $[\alpha]^{25}=-153°$ respectively, were used. These solutes are well characterized and have a high specific rotation. Solutions of 1 to 5 mM glycerol, R- or S-mandelic acid, were drawn into the channel 26 and the change in the polarimetric signal (integrated intensity of the first three fringes in the pattern) was recorded. The 0 mM is a measurement of water, which was used as a reference. The resulting plots of intensity versus concentration confirmed that increasing glycerol concentrations produce very little signal change, an exciting observation given that RI changes fundamentally limit conventional optical activity measurement techniques. The R-mandelic acid has a negative slope and the S-mandelic acid has a positive slope. The observations demonstrates that: 1) the system 10 can detect an optically active molecule whose signal increases in a concentration dependent manner; 2) the R and S enantiomers produce opposite effects in the system 10. These results show that polarimetric measurements can be made on samples contained in channels on a chip with a detection volume in the nanoliter to picoliter range.

Expanding on these observations, the system 10 was modified to employ a CCD-based laser beam analyzer (LBA) as the detector 34. The resolution of the modified system was evaluated using a micro rotation stage mounted Glan Thompson polarizer. Rotation of the polarization plane in five-degree increments yielded a function of intensity verses degree change (y=1.96E+06x+8.22E+06, R2=0.999). Then an intensity vs. concentration {R-mandelic acid at 1, 2, 3, 4, 5, 25, 50, 75, and 100 mM} plot was generated which gave a linear response (y=42532x+1E+07, $R^2$=0.991). Using these two plots the response of the OCP 10 in degree change vs. concentration was generated. The detection limit was determined using four complete and independent runs with R-mandelic acid solutions. At 3σ, the detection limit was found top be 0.018 degrees. This value is more than 4 times better than other multiplex systems (0.08 degrees). While poorer than a conventional polarimeter, the OCP 10 compares favorably given it has a probe volume 3 decades smaller.

Figure 4A:
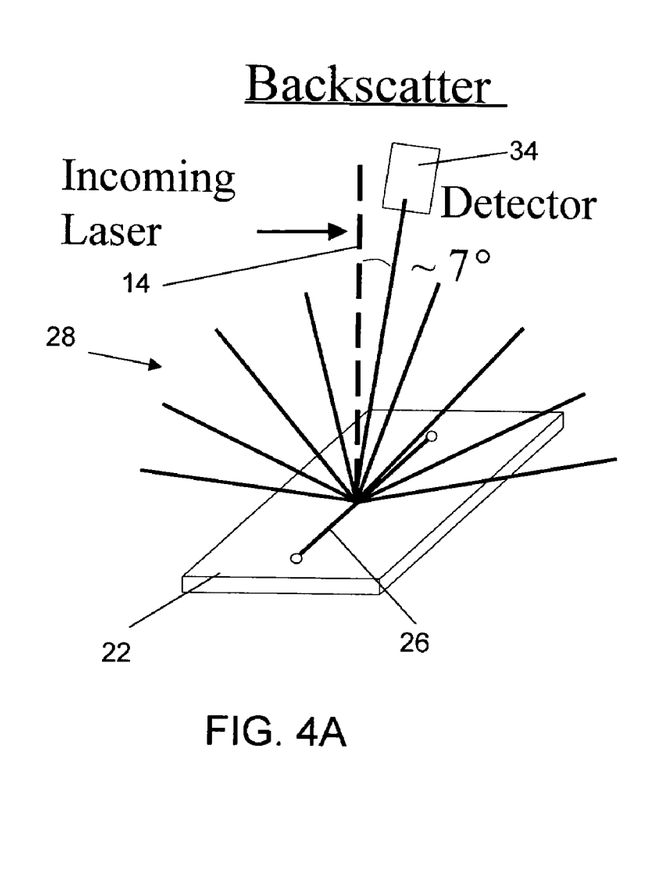
FIGS. 4A and 4B are schematic illustrations showing relative positioning of a photodetector element in direct backscatter and sidescatter detection embodiments of the present invention, respectively.
Figure 4B:
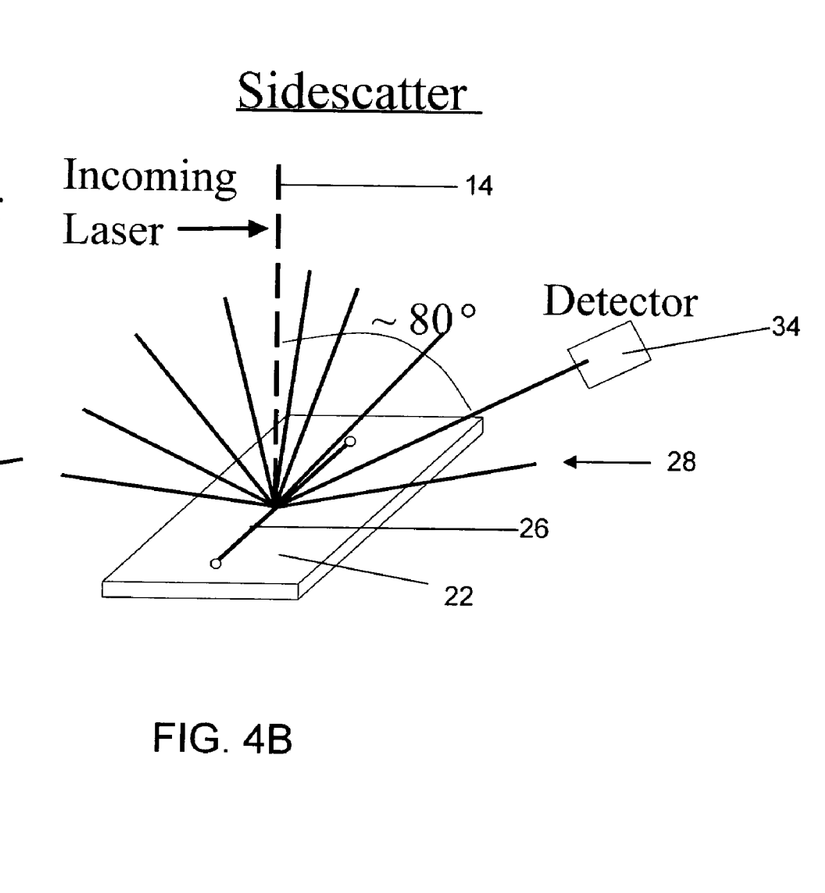

FIGS. 4A and 4B are schematic illustrations showing two different orientations that can be used for detecting the fringe patterns from the channel 26 using the system of FIG. 1. In FIG. 4A, the direct backscatter embodiment is shown in which the angle between the incident laser beam 14 and the back scattered fringe pattern beam 28 is very small, on the order of 5 to 10 degrees (7 degrees in the test embodiment). However, in FIG. 4B, the side scatter embodiment is shown in which the fringe pattern beam 28 forms an angle of between 65 and 90 degrees with the path of the incident laser beam 14, with 80 degrees being optimal for the channel used in these experiments. A cursory evaluation of the OCP interference pattern indicated that at these wider scattering angles on the order of 65-90 degrees, there are regions dominated by high frequency fringes. These high frequency fringes attenuate when the incoming polarization plane is rotated and are insensitive to refractive index changes (the position of these fringes does not change with a change in RI of the solution). Thus the side scatter embodiment of the present invention need not employ the second GT polarizer 30. In other words, this embodiment employs even simpler transduction because the absence of low frequency fringes allows the total intensity to be measured rather than extracting the polarization sensitive intensity component using the second GT polarizer 30.

Although the present sidescatter configuration does not allow the determination of absolute optical activity, it does allow the potential to discriminate between R- and S-isomers. As in the direct backscatter embodiment, rotation of the half-wave plate produced a $\cos^2$ relationship as predicted by Mauls Law. Further evaluation of the sidescatter embodiment was performed with the half-wave plate positioned at 134°. Again solutions of glycerol, R- and S-mandelic were employed. The results showed that the sidescatter embodiment has little sensitivity to RI changes, and responds oppositely to the two enantiomers as desired. Interestingly, the intensity for R-increases in this configuration for the half-wave plate. Positioning it at 44° would produce a negative slope for R-mandelic acid as before. The detection limit was determined to be 0.58 mM for R- and 0.04 mM for S-mandelic acid, which is about 20 times higher than the limit for best commercial instrument but was accomplished in a 30,000 times smaller volume.

Performing enantiomeric excess (ee) measurements in nanoliter volumes is of paramount importance and can also be accomplished using the subject on-chip polarimeter. In another experiment, a preliminary result indicated that ee could be measured using the sidescatter embodiment of the invention. Mixtures of R- and S-mandelic acid in proportions of 9:1, 7:3, 5:5, 3:7, and 1:9 (at a total solute concentration of 5 mM) were measured, as were pure solutions of the solutes. As expected, the R-mandelic acid gave the highest intensity and as the mixtures progressed to the pure S-mandelic acid, the intensity decreased. These results indicate that enantiomeric excess can be measured utilizing the on-chip polarimeter 10.

Figure 5:
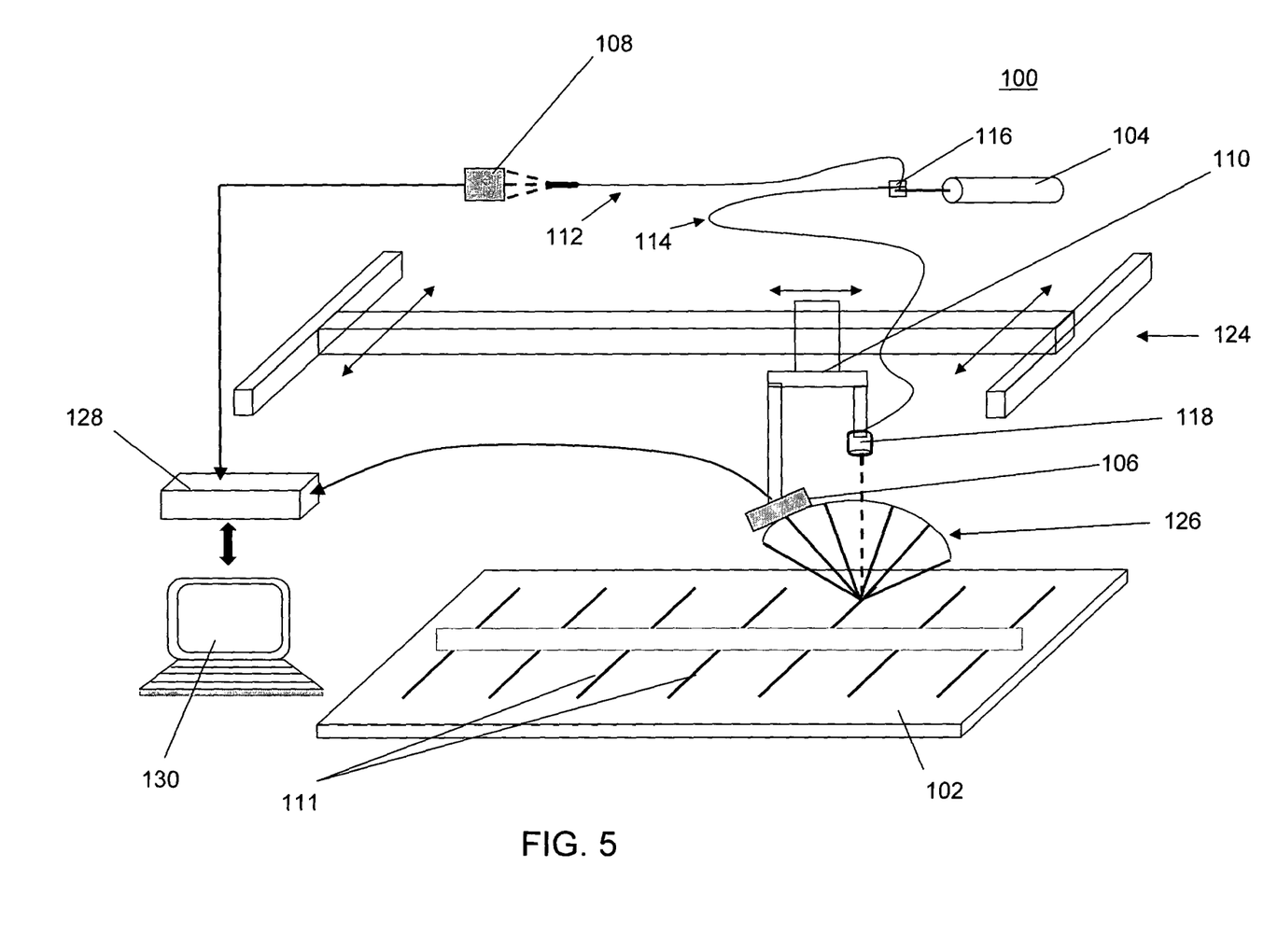
FIG. 5 is a schematic illustration of a high-throughput on-chip polarimetry system constructed in accordance with another preferred embodiment for making polarimetry measurements on multiple samples contained in multiple channels on a single chip.

With reference to FIG. 5, an HT embodiment of the present invention is illustrated that can be employed to perform multiple analyses on a single chip. An HT OCP system 100 is shown that consists of a multichannel plate 102, an illumination source 104, sample and reference detectors 106 and 108, respectively, and a moving carriage 110 capable of accurate placement in 2D.

The multichannel plate 102 contains a plurality of microfluidic channels 111 each with input and output ports (not shown) that are compatible with a standard 96-well plate so that the existing automated pipettors can be used for rapid and simple channel loading and washing. The illumination source 104 consists of a 5-10 mW linearly polarized laser (He—Ne) and is coupled to first and second optical fibers 112 and 114, respectively, with a splitter 116 that divides the total intensity between the reference and sampling arms. A small portion of the incoming laser beam is directed onto the reference detector 108 through a bifurcation in the fiber a short distance from the source. The sampling fiber terminates in an optical assembly 118 that includes a collimating lens, a high extinction polarizer, and (as needed for alignment purposes) a λ/2 plate.

This optical assembly 118 is mounted adjacent to the sample detector 106 on the carriage 110. The carriage 110 is positioned in the x and y directions using a high precision motorized translation system 124.

The computer controlled carriage 110 allows exact placement of the laser beam over each channel to create an interference fringe pattern 126 which is sensed with the sample detector 106. Output of the sample detector 106 is compared with the reference detector 108, amplified and/or filtered, digitized with a control circuit 128 and sent to a computer 130 for storage and analysis.

The HT system 100 can be used to quantify numerous parameters, including all analytical figures of merit, particularly minimal detectable quantities, S/N under various conditions and solvents, intra-channel and inter-channel reproducibility, temperature sensitivity and RI perturbation sensitivity. The system 100 can take several measurements per second and this enables the system to monitor enantioselective enzyme reactions and enzymatic conversions that produce a change in optical rotation, as the reaction occurs over time.

Kinetic constants are generally measured in the steady state; they are independent of enzyme concentration and are based on relative measurements of enzymatic conversion. A preliminary study of phenylalanine ammonia lyase (PAL) served as an initial attempt to measure Km and Vmax values with the system 10 in FIG. 1 (monitored simultaneously with UV-vis). By varying the substrate concentration and measuring the velocity of the reactions, it was possible to produce a linear response on a 1/V vs. 1/[S] graph. Km and Vmax values can be obtained from this double reciprocal plot. Thus the system described here allows kinetic information to be obtained.

In conclusion, the various embodiments of the OCP provide the ability to perform polarimetric measurements in microfluidic channels, yielding the advantages inherent in chips: 1) reduced volumes; 2) ability to integrate several functions or manipulations onto a single chip; 3) inherent compatibility for multiplexing. Unique to OCP is the relative insensitivity to RI perturbations and the potential to compensate for them using the on-chip interferometric backscatter detector (OCIBD) under circumstances where they are problematic. D/S-OCP represent a novel instrumental approach to measuring optical activity and for quantifying ee in a format that is inherently compatible with HT screening.

Although the invention has been disclosed in terms of a number of preferred embodiments and variations thereon, it will be understood that numerous other variations and modifications could be made thereto without departing from the scope of the invention as set forth in the following claims.

What is claimed is:

1. A system for measuring optical activity in a sample comprising:
a chip having a channel formed therein for reception of a sample to be analyzed;
a source of plane polarized light for generating and directing an incident beam of radiation onto said channel; and
a polarization detector for receiving interference fringe pattern radiation that is scattered by said channel and said sample when said beam of radiation is incident thereon and determining whether said scattered radiation has a plane of polarization that has been rotated relative to the plane of polarization by optically active molecules in said sample.

2. The system of claim 1, wherein said chip is formed from glass and said channel has a generally hemispherical cross section.

3. The system of claim 2, wherein said chip is formed form fused silica.

4. The system of claim 1, wherein said chip is formed from a plastic of optical quality.

5. The system of claim 4, wherein said channel has a rectangular cross section.

6. The system of claim 4, wherein said plastic is PDMS.

7. The system of claim 1, wherein said detector for receiving interference fringe pattern radiation that is scattered by said channel and said sample when said beam of radiation is incident thereon is positioned to receive side scattered radiation that is directed along an axis that is at an angle of 65-90 degrees relative to an axis of said incident laser beam, said side scattered radiation containing high frequency polarization rotation dependent components.

8. The system of claim 7, wherein said detector for receiving interference fringe pattern radiation that is scattered by said channel and said sample when said beam of radiation is incident thereon is positioned to receive radiation that is directed along an axis that is at an angle of approximately 80 degrees relative to an axis of said incident laser beam.

9. The system of claim 1, wherein said detector for receiving interference fringe pattern radiation that is scattered by said channel and said sample when said beam of radiation is incident thereon is positioned to receive radiation that is directly back scattered along an axis that is at an angle of 5-10 degrees relative to an axis of said incident laser beam.

10. The system of claim 9, wherein said detector for receiving interference fringe pattern radiation that is scattered by said channel and said sample when said beam of radiation is incident thereon is positioned to receive radiation that is directly back scattered along an axis that is at an angle of approximately 7 degrees relative to an axis of said incident laser beam.

11. The system of claim 10, wherein said source of plane polarized light for generating and directing a beam of radiation onto said channel comprises a laser and a first polarimetry plate disposed between said laser and said chip.

12. The system of claim 11, further comprising a second polarimetry plate disposed between said chip and said detector for filtering refractive index dependent low frequency components in said scattered radiation.

13. The system of claim 1, wherein said chip includes a plurality of channels formed therein for reception of a corresponding plurality of samples to be analyzed, and said source of plane polarized light and said detector are mounted on a carriage that is movable with a motorized translation system to adjust the position of said source and detector with respect to said channels.

14. The system of claim 1, wherein said detector includes a signal analyzing device for receiving said signal from said detector and determining a degree to which said scattered radiation has a plane of polarization that has been rotated relative to the plane of polarization by optically active molecules in said sample.

15. The system of claim 14, further including a beam splitter and a reference detector, said beam splitter being positioned to direct a portion of said incident beam of radiation from said source to said reference detector, which generates a signal that is fed to said analyzer and is employed by said analyzer to compensate for variations in said incident beam.

16. A method for analyzing an optically active sample comprising the steps of:
providing a chip having a channel formed therein for reception of a sample to be analyzed;
disposing a sample to be analyzed in said channel;

directing an incident beam of plane polarized light onto said channel;

detecting an interference fringe pattern that is generated by said channel and said sample when said beam of radiation is incident thereon and scattered thereby; and determining from said interference fringe pattern, whether said scattered beam of radiation has a plane of polarization that has been rotated relative to the plane of polarization by optically active molecules in said sample.

17. The method of claim 16, wherein the step of providing said chip comprises providing a chip that is made from a material selected from the group comprising glass, plastic, fused silica and PDMS.

18. The method of claim 16, wherein the step of detecting an interference fringe pattern comprises positioning an optical detector to receive side scattered radiation that is directed along an axis that is at an angle of 65-90 degrees relative to an axis of said incident laser beam, said side scattered radiation containing high frequency polarization rotation dependent components.

19. The method of claim 18, wherein said detector for receiving interference fringe pattern radiation that is scattered by said channel and said sample when said beam of radiation is incident thereon is positioned to receive radiation that is directed along an axis that is at an angle of approximately 80 degrees relative to an axis of said incident laser beam.

20. The method of claim 16, wherein the step of detecting an interference fringe pattern comprises positioning an optical detector to receive radiation that is directly back scattered along an axis that is at an angle of 5-10 degrees relative to an axis of said incident laser beam.

21. The method of claim 20, wherein said detector for receiving interference fringe pattern radiation that is scattered by said channel and said sample when said beam of radiation is incident thereon is positioned to receive radiation that is directly back scattered along an axis that is at an angle of approximately 7 degrees relative to an axis of said incident laser beam.

22. The method of claim 21, wherein said step of directing an incident beam of plane polarized light onto said channel comprises directing said incident beam from a laser through a first polarimetry plate and onto said channel.

23. The method of claim 22, further comprising the step of positioning a second polarimetry plate between said chip and said detector for filtering refractive index dependent low frequency components in said scattered radiation.

* * * * *